United States Patent [19]

Venkatasetty

[11] Patent Number: 4,522,690
[45] Date of Patent: Jun. 11, 1985

[54] ELECTROCHEMICAL SENSING OF CARBON MONOXIDE

[75] Inventor: Hanumanthaiya V. Venkatasetty, Burnsville, Minn.

[73] Assignee: Honeywell Inc., Minneapolis, Minn.

[21] Appl. No.: 557,072

[22] Filed: Dec. 1, 1983

[51] Int. Cl.³ ............................................. G01N 27/46
[52] U.S. Cl. .................................. 204/1 T; 204/412; 204/414; 204/415
[58] Field of Search ............ 204/1 T, 1 K, 1 N, 1 F, 204/415, 400, 414, 412

[56] References Cited

U.S. PATENT DOCUMENTS

| | | | |
|---|---|---|---|
| 3,260,656 | 7/1966 | Ross | 204/415 |
| 3,833,495 | 9/1974 | Grubb | 204/414 |
| 4,049,503 | 9/1977 | Becker et al. | 204/1 F |
| 4,141,800 | 2/1979 | Breuer et al. | 204/1 K |
| 4,149,948 | 4/1979 | Petersen et al. | 204/1 F |
| 4,169,779 | 10/1979 | Tataria et al. | 204/415 |
| 4,197,176 | 4/1980 | Ensanian | 204/414 |
| 4,394,239 | 7/1983 | Kitzelmann et al. | 204/414 |

*Primary Examiner*—T. Tung
*Attorney, Agent, or Firm*—Charles G. Mersereau

[57] ABSTRACT

Apparatus and method for an electrochemical sensor for carbon monoxide detection in a gelled aprotic organic nonaqueous electrolyte solution.

17 Claims, 6 Drawing Figures

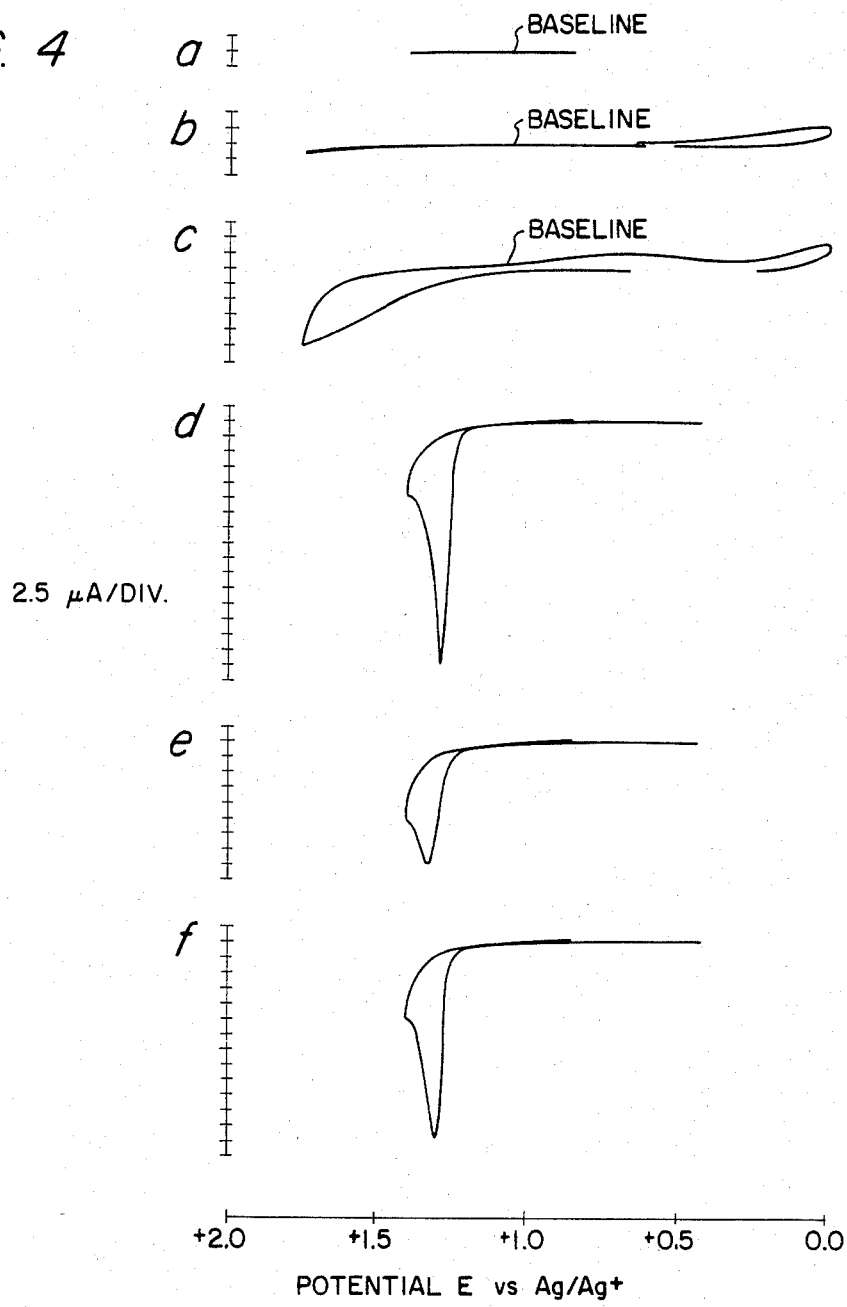

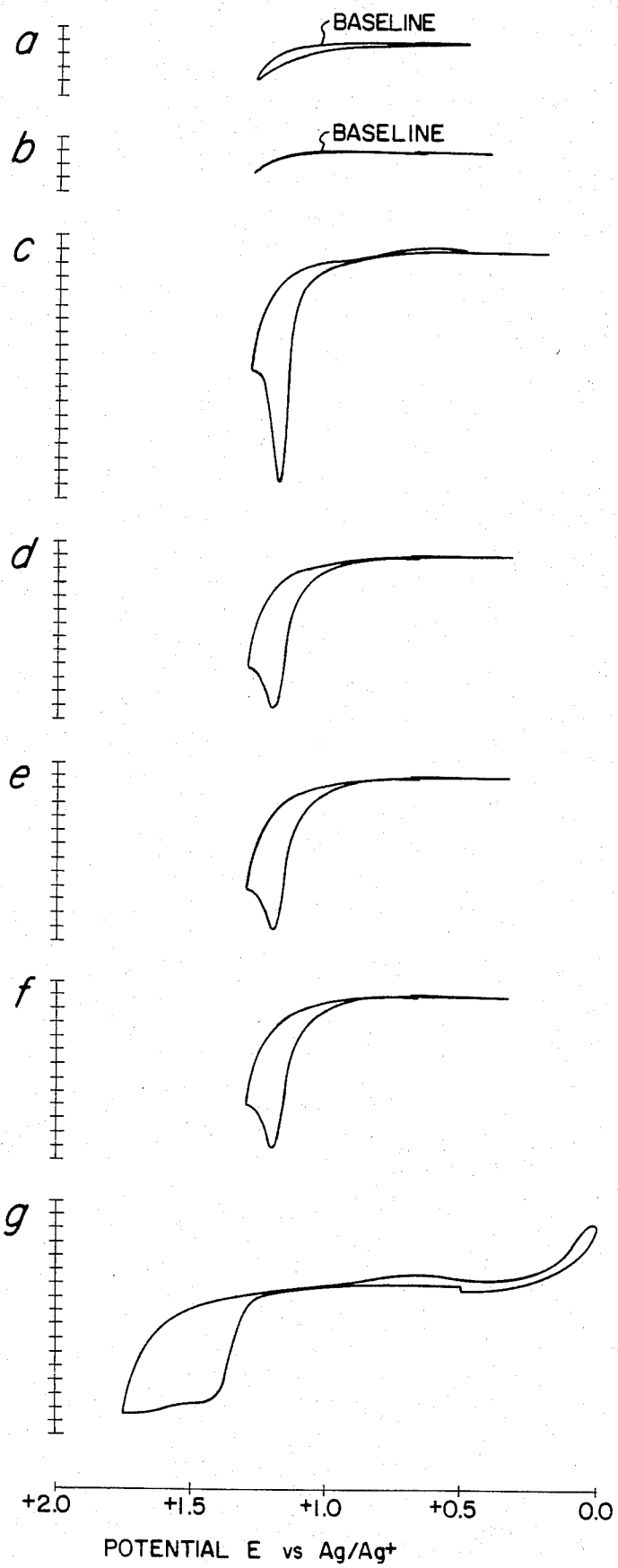

ELECTROCHEMICAL SENSING OF CARBON MONOXIDE

CROSS REFERENCE TO RELATED APPLICATION

Cross reference is made to application Ser. No. 557,037, filed of even date, entitled "An Electrochemical Sensor for Multiagent Detection in Aprotic Organic Electrolyte Solution" and now abandoned. That application also is by H. V. Venkatasetty, the inventor in this application and is assigned to the same assignee as the present application.

That invention involves an electrochemical cell utilizing nonaqueous electrolyte solutions with aprotic solvents. An electrochemical oxidation process at the platinum electrode is employed for the detection of small amounts of chemical agent simulants such as dimethyl methyl phosphonate (DMMP) and diethyl malonate (DEM) in the electrolyte solution. Electrolyte solutions include propylene carbonate or γ-butyrolactone containing lithium perchlorate or tetraethylammonium perchlorate.

The present invention, on the other hand, involves the detection of carbon monoxide (CO) electrochemically using a gelled electrolyte containing an amount of polyethylene oxide. An electrolyte solution of approximately 1.0M lithium perchlorate ($LiClO_4$) in γ-butyrolactone or approximately 0.75M $LiClO_4$ in propylene carbonate when gelled with polyethylene oxide has been found to be especially suited to the detection of CO by oxidation at the platinum electrode.

BACKGROUND OF THE INVENTION

Electrochemical reactions based on oxidation or reduction (redox) of metals and compounds at an electrode are highly selective because of the characteristic redox potential at which oxidation or reduction of the electroactive species occurs. With electrochemical sensing, selection of the electrode material and electrolyte solution has been very important in determining sensitivity and selectivity. A detailed description of the theoretical considerations is contained in the above cross-referenced application and is incorporated by reference in this application to the extent required.

One limitation of the prior art is that the presence of hydrogen ions, either in the solvent or in the additive (electrolyte), will interfere with the oxidation and reduction of chemical agents sought to be detected. This had lead to the necessity for developing aprotic (free of replaceable hydrogen ions) electrolyte systems.

SUMMARY OF THE INVENTION

By means of the present invention, an electrochemical detection system has been developed which is extremely sensitive to the presence of CO and can also be used to detect other toxic gases such as nitrogen oxides ($N_2O_4$, $NO_x$) $SO_2$, $H_2S$ and the like.

The system includes a nonaqueous, aprotic electrolyte system of approximately 1.0M $LiClO_4$ in γ-butyrolactone or approximately 0.75M $LiClO_4$ in propylene carbonate gelled with a small amount of polyethylene oxide (about 1% by weight based on the other constituents). A platinum electrode is used on the oxidation site for the gas detection. The polymer containing electrolyte solutions have high electrolytic conductivity, low vapor pressure, high solubility for carbon monoxide and high chemical and electrochemical stability.

The electrolyte solution and electrodes can be packaged into a low-cost electrochemical cell for detecting carbon monoxide or other gases using a semipermeable membrane coated on one side with platinum metal film as the sensing electrode. The polymer based electrolyte solution can be easily contained in the cell assuring long shelf life.

BRIEF DESCRIPTION OF THE DRAWINGS

FIGS. 4 and 5 show graphical plots of the sensor response to CO.

DESCRIPTION OF THE PREFERRED EMBODIMENT

Figure 1:
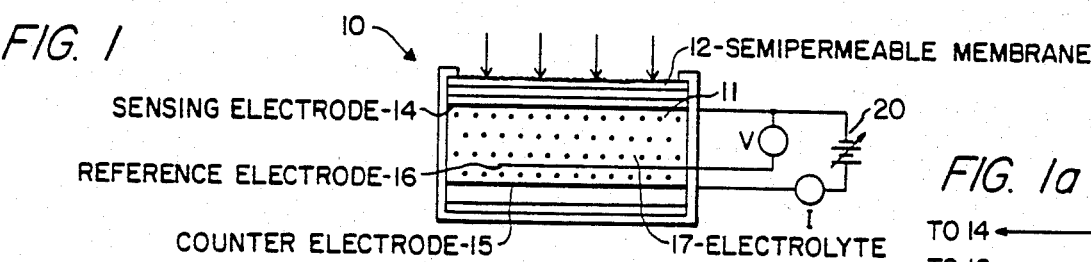
FIGS. 1 and 1a are schematic diagrams of an electrochemical cell for demonstrating the invention.
Figure 1A:
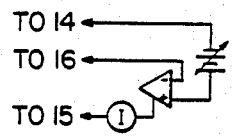

FIG. 1 generally illustrates an electrochemical cell 10 consisting of a chamber 11 having a semipermeable membrane 12 across an opening. The chamber 11 contains a film of platinum working or sensing electrode 14, a counter electrode 15 of platinum film and a Ag/Ag+ reference electrode 16. An adjustable potential source 20 is connected across the sensing and counter electrode and the current is measured. A voltage exists but no current flows from the reference electrode to the sensing electrode. A preferred form of this energizing circuit may include an operational amplifier as shown in FIG. 1a wherein no current flows in the feedback loop from the reference electrode to the negative input of the operational amplifier. The three electrodes are internally separated by a material which also acts as a wicking material for the electrolyte.

A gelled nonaqueous electrolyte solution 17 permeates and fills the chamber. This solution utilizes an aprotic organic solvent such as propylene carbonate or γ-butyrolactone and an active electrolyte such as $LiClO_4$ which has a wide potential window so that gases sought to be detected can be oxidized or reduced without decomposing the electrolyte solution.

A previously stated, the electrolyte solvent should be aprotic (no replaceable hydrogen atoms) and it should have a high boiling point, low freezing point to provide a wide operating temperature range between boiling point and freezing point, and low vapor pressure so that it is stable. The solvent should have a fairly high dielectric constant and low viscosity so that the solutes are easily soluble, giving solutions with fairly high conductivity. The solvent and electrolyte solutions from such solvents should be electrochemically stable to oxidation and reduction, giving a wide voltage window to carry out electrochemical redox reactions at an electrode surface. The solvent should be low cost, should be easily purified, and should be nontoxic. The following solvents have been chosen for the electrolyte system of the invention.

| Properties | Propylene Carbonate | γ-Butyrolactone |
|---|---|---|
| Boiling point (°C.) | 241 | 202 |
| Freezing point (°C.) | −49 | −43 |
| Dielectric constant | 64.4(25° C.) | 39(20° C.) |

| Properties | Propylene Carbonate | γ-Butyrolactone |
|---|---|---|
| Viscosity mP (25° C.) | 25.3 | 17.5 |
| Density (25° C.) g/ml | 1.19 | 1.13 |

Figure 2:
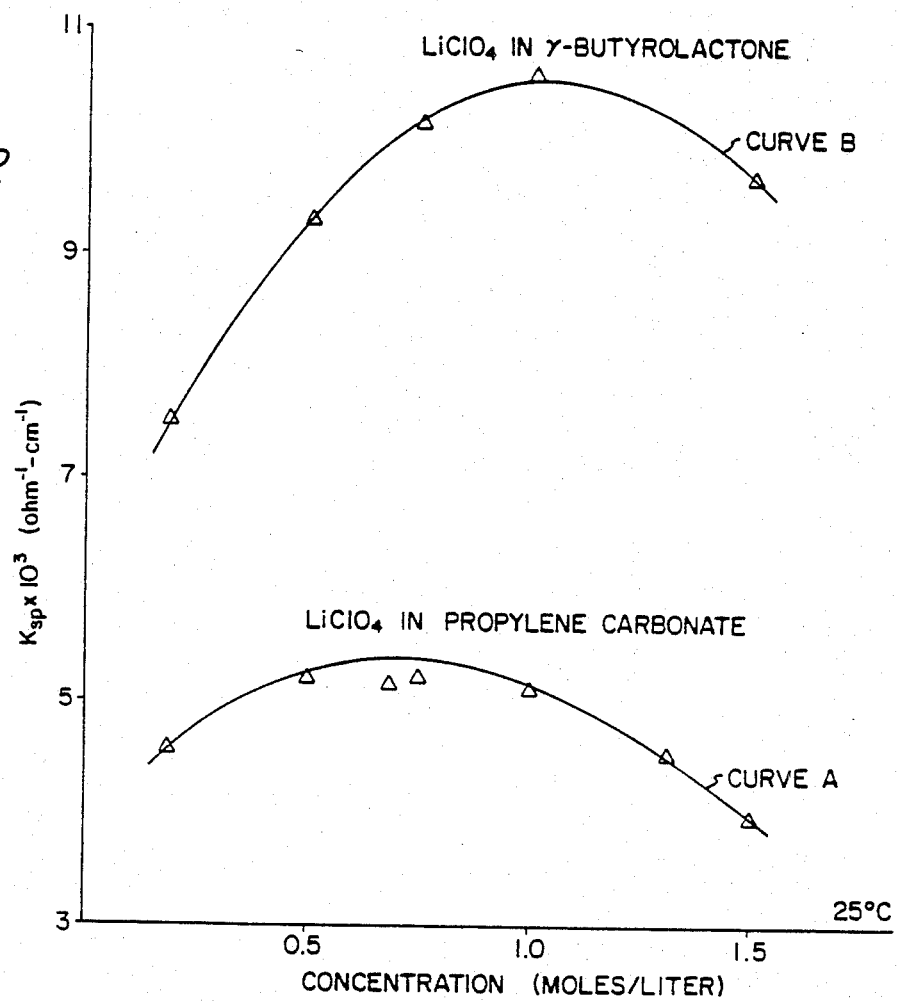
FIG. 2 is a graphical presentation of specific conductance vs. concentration (25° C.) of several electrolytes in nonaqueous solvents.

The conductivity concentration studies carried out using lithium perchlorate solute as the supporting electrolyte in propylene carbonate show a maximum conductivity at about 0.75M (FIG. 2, curva A) whereas similar studies in the preferred γ-butyrolactone show a much higher maximum conductivity at about 1M (FIG. 2, curve B). As seen from the above, solvents such as propylene carbonate or γ-butyrolactone have a high boiling point, low melting point, and very low vapor pressure. They are also non-corrosive so that the electrochemical cell can operate over a wide temperature range for an extended period. Gases such as CO are highly soluble in these nonaqueous organic solvents making for high sensitivity of detection.

With the wide range of potential window available for oxidation and reduction, many gases can be oxidized or reduced in the same cell so that the electrochemical cell can be used for different gases of interest.

The electrochemical method for the quantitative determination of materials is based on the principle of limiting current density measured at the electrode surface. Limiting current density is defined as the current density resulting from the oxidation or reduction of every molecule of the electroactive material or chemical agent reaching the electrode surface. A linear relationship between the limiting current density ($i_L$) and the bulk concentration ($C_b$) of the electroactive material or chemical agent can be obtained using Fick's law of diffusion $$i_L = nFDC_b/\partial$$

where D is the diffusion coefficient of the electroactive molecules in the electrolyte, n is the number of electrons involved, F is the Faraday constant, and $\partial$ is the diffusion layer thickness. Thus, the limiting current density provides the quantitative measure of the concentration, while the characteristic redox potential identifies the molecules.

Figure 3:
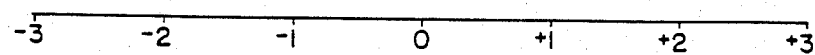
FIG. 3 is a graphical presentation of potential ranges available in nonaqueous vs. aqueous electrolyte solutions.
Figure 3:
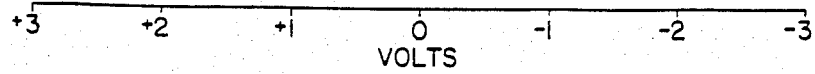

FIG. 3 shows graphically a sample comparison of potential ranges available in nonaqueous vs. aqueous electrolyte solutions. Aqueous electrolytes are limited to a voltage range of about 1.5 volts of redox potential as shown in the figure. The presence of protons in aqueous based electrolytes interferes with redox processes of organic molecules, even within this range. Aprotic electrolytes (nonaqueous) contain no protons and can achieve three times the voltage range of aqueous electrolytes, or about 4.5 volts as shown. Nonaqueous organic electrolytes are preferable for the analysis of CO and organic compounds such as chemical agents which are more soluble in organic electrolyte solutions compared to aqueous electrolyte solutions.

Electrochemical experiments have been conducted to demonstrate the feasibility of nonaqueous electrochemical redox techniques for the detection and identification of simulants for chemical agents. Concentrated solutions of supporting electrolytes such as 0.5M lithium perchlorate ($LiClO_4$) and 0.1M tetraethylammonium perchlorate (TEAP) in propylene carbonate (PC) or γ-butyrolactone were prepared and used in a conventional electrochemical setup. The sensing and counter electrodes were platinum and the reference electrode was $Ag/Ag+$. The preferred solvent was γ-butyrolactone. The preferred electrolyte/solvent system is 1M $LiClO_4$ in γ-butyrolactone. The electrochemical instrumentation consisted of a Princeton Applied Research Model 173 potentiostat/galvanostat with a Model 175 Universal Programmer, Model 179 digital Coulometer, and Hewlett-Packard Model 7040A x-y recorder.

The gelled nonaqueous electrolyte solution is prepared by dissolving 1% (by wt.) of the polymer, polyethylene oxide (Molecular weight approximately 100,000) in 1.0M $LiClO_4$ in γ-butyrolactone or 0.75M $LiClO_4$ in propylene carbonate. The solution in γ-butyrolactone has specific conductivity of $9.89 \times 10^{-3}$ ohm$^{-1}$ cm$^{-1}$ whereas the solution in propylene carbonate has specific conductivity of $5.389 \times 10^{-3}$ ohm$^{-1}$ cm$^{-1}$ at 25° C. These solutions can be used as media for the dissolution of carbon monoxide gas and the carbon monoxide gas can be oxidized at the platinum electrode surface at a known potential. In the case of propylene carbonate solution, carbon monoxide can be oxidized at +1.25 to +1.30 V VsAg/Ag+ whereas in γ-butyrolactone solution, carbon monoxide can be oxidized at +1.20 V VsAg/Ag+. This is illustrated in FIGS. 4 and 5, respectively. The oxidation shown beyond 1.3 V (curve f of FIG. 4) and 1.2 V (curve g of FIG. 5) are due to oxidation of other components at higher potentials. The very sharp, distinct change in current is very accurate and repeatable. The current generated at these oxidation potential(s) is proportional to the concentration of carbon monoxide in the electrolyte solution. These electrolyte solutions are stable to electrochemical oxidation and reduction within the potential range of interest to carbon monoxide detection.

The gelled electrolyte solutions do not flow through semipermeable membranes like PTFE (polytetrafluoroethylene) that are used in low cost carbon monoxide sensors and, therefore, the cells can be made to last longer. The polymer containing electrolyte solutions can be packaged easily for sensing CO.

While the invention has been particularly described with reference to CO, other gases such as oxide of nitrogen ($N_2O_4$, $NO_x$) and gases such as $SO_2$ and $H_2S$ should produce distinct results also. The three electrode configuration cell structure shown in FIG. 1 is set up with a small amount of the electrolyte solution (~1 cc) with arrangement to apply a known potential and measuring the current generated. The carbon monoxide gas is allowed to enter the cell through the semipermeable membrane and establish equilibrium state. By applying a potential slightly higher than the oxidation value, the electroactive species, namely CO around the sensing anode is completely oxidized and the current-concentration relationship can be established according to the relationship.

The embodiments of the invention in which an exclusive property or right is claimed are defined as follows:

1. A method for detecting the presence of a plurality of toxic agents comprising the steps of:
    providing electrochemical cell means having an electrode configuration comprising a plurality of electrodes including a platinum working electrode, a platinum counter electrode and an Ag/Ag+ reference electrode;
    providing a nonaqueous gelled aprotic electrolyte solution in the electrochemical cell means, said solution comprising an aprotic organic solvent selected from the group consisting of γ-butyrolactone and propylene carbonate, an amount of lithium perchlorate electrolyte and polyethylene oxide gelling agent;

exposing the electrochemical cell means to an atmosphere suspected of containing the gas of interest;

providing electrical source means and connecting the source means to the electrode configuration to energize the cell means; and providing means for measuring the current flowing between said sensing electrode and said counter electrode.

2. An electrochemical sensor for toxic gas detection comprising:

electrochemical cell means having therein an electrode configuration comprising a plurality of electrodes including a platinum working electrode, a platinum counter electrode and an Ag/Ag+ reference electrode;

a nonaqueous gelled aprotic electrolyte solution in said cell means, said electrolyte solution comprising an aprotic organic solvent selected from the group consisting of γ-butyrolactone and propylene carbonate, an amount of lithium perchlorate electrolyte and an amount of polyethylene oxide gelling agent;

adjustable potential electrical source means, to energize said electrochemical cell means at desired potentials, connected across said working and counter electrodes; and current measuring means connected across said working and counter electrodes.

3. The sensor of claim 2 wherein the nonaqueous electrolyte solvent is γ-butyrolactone.

4. The sensor of claim 3 wherein the concentration of lithium perchlorate is about 1.0M.

5. The sensor of claim 4 wherein the amount of said polyethylene oxide is about 1% by weight based on the weight of the solution.

6. The sensor of claim 5 wherein said toxic gas to be detected is CO.

7. The sensor of claim 2 wherein said working and counter electrodes are in the form of a thin platinum film.

8. The sensor of claim 2 wherein the nonaqueous electrolyte solvent is propylene carbonate.

9. The sensor of claim 8 wherein the concentration of the electrolyte is about 0.75M.

10. The sensor of claim 9 wherein the amount of said polyethylene oxide is about 1% by weight based on the weight of the solution.

11. The sensor of claim 10 wherein said toxic gas to be detected is CO.

12. An electrochemical sensor for toxic gas detection comprising:

electrochemical cell means having therein an electrode configuration comprising a plurality of electrodes including a platinum electrode working, a platinum counter electrode and an Ag/Ag+ reference electrode;

a nonaqueous gelled aprotic electrolyte solution in said cell means, said solution comprising an aprotic organic solvent selected from the group consisting of γ-butyrolactone and propylene carbonate, an electrolyte comprising an amount of lithium perchlorate and an amount of tetraethylammonium perchlorate and an amount of polyethylene oxide gelling agent;

adjustable potential electrical source means, to energize said electrochemical cell means at desired potentials, connected across said working and counter electrodes; and current measuring means connected across said working and counter electrodes.

13. The sensor of claim 12 wherein the non-aqueous electrolyte solvent is γ-butyrolactone.

14. The sensor of claim 13 wherein the concentration of said tetraethylammonium perchlorate is about 0.1M.

15. The sensor of claim 14 wherein the amount of said polyethylene oxide is about 1% by weight based on the weight of the solution.

16. The sensor of claim 14 wherein the toxic gas to be detected is CO.

17. The sensor of claim 12 wherein said working and counter electrodes are in the form of a thin platinum film.

* * * * *